United States Patent [19]

Cheng et al.

[11] Patent Number: 4,865,848
[45] Date of Patent: Sep. 12, 1989

[54] SKIN PERMEATION ENHANCER COMPOSITIONS USING SUCROSE ESTERS

[75] Inventors: Yu-Ling Cheng, Cupertino; Robert M. Gale, Los Altos; Edna Sugihara, Mountain View; Harold F. Sanders, San Jose, all of Calif.

[73] Assignee: ALZA Corporation, Palo Alto, Calif.

[21] Appl. No.: 19,442

[22] Filed: Feb. 26, 1987

[51] Int. Cl.[4] .............................................. A61F 13/00
[52] U.S. Cl. ...................................... 424/449; 424/448
[58] Field of Search ............... 424/448, 449; 514/946, 514/947

[56] References Cited

U.S. PATENT DOCUMENTS

| | | | |
|---|---|---|---|
| 2,893,990 | 7/1959 | Hass et al. | 260/234 |
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,882,243 | 5/1975 | Maeda et al. | 424/312 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 514/171 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,568,343 | 2/1986 | Leeper et al. | 604/896 |

FOREIGN PATENT DOCUMENTS

| | | |
|---|---|---|
| 0057462 | 2/1982 | European Pat. Off. |
| 2241667 | 3/1973 | Fed. Rep. of Germany |
| 1001949 | 8/1965 | United Kingdom |

OTHER PUBLICATIONS

Idson, B., "Percutaneous Absorption", Journal of Pharmaceutical Sciences, vol. 64, No. 6 (Jun. 1975), pp. 901–924.

Chem. Abs., vol. 90, No. 2, #90: 12218y "Surfactants in Suspension. II. Model Experiments in Vitro," Duckova et al.

Chem. Abs., vol. 85, No. 24, #85: 182265a "Shampoos," Minagawa.

Primary Examiner—Thurman K. Page
Assistant Examiner—Leon R. Horne
Attorney, Agent, or Firm—Steven F. Stone; Edward L. Mandell; Paul L. Sabatine

[57] ABSTRACT

A method for enhancing the transdermal flux of a transdermally deliverable drug through intact skin is described in which the drug is delivered simultaneously with sucrose monolaurate or a mixture of sucrose esters of coconut fatty acids, which is predominantly sucrose monolaurate. Preferred embodiments of therapeutic systems for delivering the drug and the sucrose ester employ a matrix containing drug at a concentration above saturation.

3 Claims, 1 Drawing Sheet

SKIN PERMEATION ENHANCER COMPOSITIONS USING SUCROSE ESTERS

FIELD OF THE INVENTION

This invention relates to the transdermal delivery of drugs or other biologically active agents and more particularly to novel methods and compositions for enhancing the permeability of skin or other body surfaces to biologically active agents.

RELATED PATENT APPLICATIONS

This invention is related to the inventions disclosed in copending, coassigned patent applications of Gale, et al for Transdermal Administration of Progesterone, Estradiol Esters and Mixtures thereof, U.S. Ser. No. 07/019,162 of Cheng, et al for Skin Permeation Enhancer Compositions Using Glycerol Monolaurate, U.S. Ser. No. 07/019,407 and of Nedberge, et al for Transdermal Contraceptive Formulations, U.S. Ser. No. 07/019,163 all of like date herewith.

BACKGROUND OF THE INVENTION

The transdermal route of parenteral delivery of drugs provides many advantages and transdermal systems for delivering a wide variety of drugs or other beneficial agents are described in U.S. Pat. Nos. 3,598,122, 3,598,123, 4,379,454, 4,286,592, 4,314,557 and 4,568,343 for example, all of which are incorporated herein by reference. In many cases, drugs which would appear to be ideal candidates for transdermal delivery are found to have such low permeability through intact skin that they cannot be delivered at therapeutically effective rates from reasonably sized systems. In an effort to increase skin permeability it has been proposed to pretreat the skin with various chemicals or to concurrently deliver the drug in the presence of a permeation enhancer. Various materials have been suggested for this purpose as described in U.S. Pat. Nos. 4,299,826, 4,343,798, 4,046,886, 4,130,643, 4,405,616, 4,335,115, 4,130,667, 3,903,256, 4,379,454, 3,527,864, 3,952,099, 3,896,238, 3,472,931 all of which are incorporated herein by reference, British Pat. No. 1,001,949 and Idson, Percutaneous Absorption, J. Phar. Sci., Vol. 64, No. b6, June 1975, pp. 901-924 (particularly 919-921). To be considered useful a permeation enhancer should possess certain characteristics in addition to its ability to enhance the permeability of at least one and preferably a large number of drugs. These characteristics include being non-toxic, non-irritating on prolonged exposure and under occlusion, and non-sensitizing on repeated exposure. Preferably it should also be odorless and capable of delivering drugs without producing burning or tingling sensations.

According to our invention, we have discovered that sucrose esters and in particular sucrose monolaurate (SML), are effective in enhancing the permeation of several drugs and other therapeutic or beneficial agents through body surfaces and membranes, generally, and skin, particularly, and when formulated in pharmaceutical compositions with other materials appears to satisfy the criteria noted above.

As noted above, the preferred sucrose ester is SML. It has been determined that the $C_{12}$ ester is most useful. For the sucrose esters, the $C_{12}$ is sucrose monolaurate. Alternately, instead of using SML alone, mixtures of the sucrose esters of coconut fatty acids, which are predominantly comprised of SML are also suitable. A readily available source of one such SML predominating mixture is SUCROSE MONOCOCOATE, commercially available from Croda, Inc. (N.J.), which is an ester mixture, with $C_{12}$ predominating.

It is accordingly an object of our invention to increase the permeability of body surfaces of animals and humans, including the mucosa and other membranes and more particularly of human sin, to the transport of drugs and other beneficial agents by the concurrent application of the drug or beneficial agent and SML to the body surface.

It is another object of our invention to provide compositions of matter for application to the skin which comprise SML and a transdermally deliverable drug or beneficial agent.

It is another object of our invention to provide transdermal therapeutic systems for the concurrent delivery of SML and a drug or beneficial agent.

These and other objects and advantages will be readily apparent from the following description with reference to the accompanying drawings wherein:

DESCRIPTION OF THE INVENTION

Figure 1:
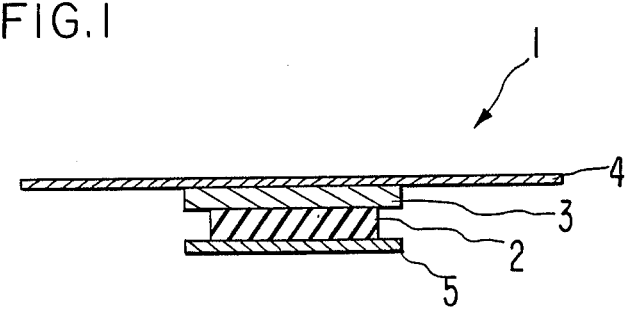
FIG. 1 is a cross-sectional view of one embodiment of the transdermal therapeutic system according to this invention.

According to our invention we have discovered that SML can be used to enhance the permeability to drugs and other beneficial agents of body surfaces generally and, more particularly, to enhance the transdermal permeability of a multiplicity of drugs useful in the treatment of a wide variety of conditions and indications. As used herein the term "drug" relates to a biologically active agent, compound or composition of matter which is administered for the purpose of providing some beneficial or therapeutic effect. As used herein the term "transdermal'" delivery relates to the delivery of a drug by passage through intact skin into the vascularized layers below the stratum corneum for absorption by the blood stream. Thus transdermal delivery is distinguished from topical application to the surface of intact skin for topical treatment or to application to open wounds or to skin lacking the stratum corneum such as burned or abraded skin. As used herein the term "SML" relates to sucrose monolaurate alone or to a mixture of sucrose esters of coconut fatty acids, with sucrose monolaurate predominating.

According to our invention a permeation enhancing sucrose ester and the biologically active agent (drug) to be delivered are placed in drug and permeation enhancer transmitting relationship to the appropriate body surface, preferably in a carrier therefor, and maintained in place for the desired period of time. The drug and SML are typically dispersed together within a physiologically compatible matrix or carrier as more fully described below which may be applied directly to the body as an ointment, gel, cream, suppository or sublingual or buccal tablet for example but are more preferably administered from a transdermal therapeutic system as more fully described below.

We have also found that SML in addition to its known low toxicity and colorless and odorless nature, does not sensitize skin on repeated exposure. Further, SML can be applied to the skin in compositions that do not produce irritation even on occlusion and repeated application to the same site and is capable of enhancing drug flux without producing objectionable skin sensations.

SML has utility in connection with the delivery of drugs within the broad class normally delivered through body surfaces and membranes, including skin. In general, this includes therapeutic agents in all of the major therapeutic areas including, but not limited to, anti-infectives, such as antibiotics and antiviral agents, analgesics and analgesic combinations, anorexics, anthemidines, antiarthritics, antiasthmatic agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, betablockers, antiarrythmics, antihypertensives, diuretics, vasodilators including general, coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

We have demonstrated the utility of SML as a permeation enhancer for a large number of dissimilar drugs within these classes, such as estradiol, hydrocortisone, progesterone, estradiol valerate, ouabain, levorphanol, morphine, hydromorphone and methadone. Additionally, we believe it to be applicable to an even larger number of such drugs including, by way of example and not for purposes of limitation; scopolamine, isosorbide dinitrate, nitroglycerin, clonidine, cortisone, theophylline, phenylephrine, terbutaline, ephedrine, narcotine, quinidine, estradiol diacetate, pilocarpine, furosemide, tetracycline, insulin, chlorpheniramine, sulfathiazides, propranolol, testosterone, norgestrel, lidocaine, morphinone, dihydrocodeine, dihydromorphine, oxycodone, hydrocodone, codeine, norcodeine, hydromorphine, normophine, norlevorphanol, dihydrothebaine, bromocryptine, guanabenz, salbutamol, oxprenolol, tetracaine, dibucaine, altenolol, pindolol, and timolol, for example as well as to other drugs not specifically noted herein.

The effect of SML as a permeation enhancer for other drugs not specifically set forth herein, may be readily determined by a worker skilled in the art from in vitro permeation measurements performed on cadaver skins or other membranes in conventional diffusion cell tests as well as by in vivo measurements of blood or urine levels for example.

SML has a permeation enhancing effect on the transport of drugs through body surface tissues generally in addition to the skin. Nevertheless, because skin is one of the most effective of the body's barriers to permeation of foreign substances, the effect of SML on skin permeation makes it extremely useful in transdermal drug delivery. The following description of preferred embodiments of the invention is therefore directed primarily to improving transdermal delivery of drugs.

Referring now to FIG. 1, a transdermal therapeutic system 1 according to this invention is shown which comprises a drug/permeation enhancer reservoir 2 in the form of a matrix containing the drug and permeation enhancer. The reservoir 2 is covered by an impermeable backing 3 which is preferably sized slightly larger in circumference than reservoir 2. Means 4 for maintaining the system on the skin may either be fabricated together with or provided separately from the remaining elements of the system which means in the embodiment of FIG. 1 takes the form of an adhesive overlay. An adhesive overlay is used with this invention because sucrose esters adversely affect the adhesive properties of most pharmaceutically acceptable contact adhesives. For this reason, impermeable backing layer 3 is preferably sized slightly larger than the reservoir 2 to provide a peripheral area around reservoir 2 free of the sucrose ester permeation enhancer, to prevent adverse interaction between the adhesive in the overlay 4 and any of the enhancer which may seep from under the base of reservoir 2 in use. A strippable release liner 5, adapted to be removed prior to application would normally be included in the packaged product.

Various materials suited for the fabrication of the various layers are disclosed in the aforementioned patents. The composition of the matrix may, depending on the drug to be delivered, be either an aqueous or anhydrous base. Suitable matrices or carriers are described in the above identified patents, and include, without limitation, natural and synthetic rubbers such as polybutylene, polyisobutylene, polybutadiene, polyethylene, styrenebutadiene, copolymers, polyisoprene, polyurethane, ethylene/propylene copolymers, polyalkylacrylate polymers, copolyesters, ethylene/acrylic copolymers, silicones and butadiene/acrylonitrile copolymers for example and other polymers such as the ethylene vinylacetate (EVA) polymers described in U.S. Pat. No. 4,144,317 (which is incorporated herein by reference), for example, gelled or thickened mineral oil, petroleum jelly and various aqueous gels and hydrophilic polymers. Typically the drug is dispersed through the matrix or carrier at a concentration in excess of saturation, the amount of the excess being a function of the intended useful life of the system. The drug, however, may be present at initial levels below saturation without departing from this invention. The enhancer is preferably dispersed through the matrix at a concentration sufficient to provide permeation enhancing concentrations of SML in the reservoir throughout the anticipated administration time, but below irritability concentration.

In addition to the drug and permeation enhancer, which are essential to the invention, the matrix may also contain other materials such as dyes, pigments, inert fillers or other permeation enhancers, excipients, and conventional components of pharmaceutical products o transdermal therapeutic systems as known to the art.

Figure 2:
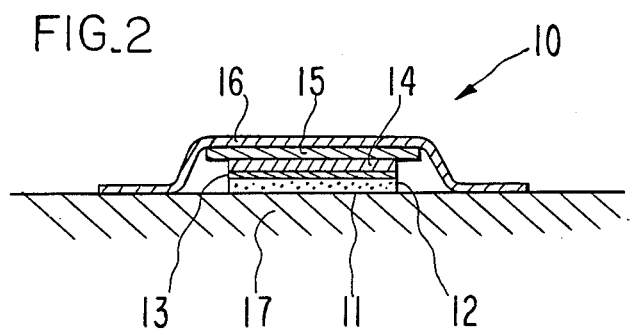
FIG. 2 is cross-sectional view of another embodiment of the transdermal therapeutic system according to this invention.

Referring now to FIG. 2 another embodiment of this invention is shown in place upon the skin 17 of a patient. In this embodiment the transdermal therapeutic system 10 comprises a multilaminate drug/enhancer reservoir 11 having at least two zones 12 and 14. Zone 12 consists of a drug reservoir substantially as described with respect FIG. 1. Zone 14 comprises a permeation enhancer reservoir which is preferably made from substantially the same matrix as used to form zone 12 and which is substantially free of any undissolved drug. A ratecontrolling membrane 13 for controlling the release rate of the SML from zone 12 to the skin may also be utilized between zones 12 and 14 if desired. Suitable rate-con trolling membranes may be formed from polymers having a permeability to SML lower than that of zone 12.

An advantage of the system described in FIG. 2 is that the drug loaded zone 12 is concentrated at the skin surface rather than throughout the entire mass of the reservoir. This functions to reduce the amount of drug in the system while maintaining an adequate permeation enhancer supply.

Superimposed over the drug/enhancer reservoir 11 is an impermeable backing 15 and adhesive overlay 16 as described above with respect to FIG. 1. In addition, a strippable release liner (not shown) would preferably be provided o the system prior to use as described with respect to FIG. 1 and removed prior to application to the skin 17.

With both FIGS. 1 and 2, the adhesive overlays can be eliminated if the skin contacting layer can be made adhesive. Use of such an in-line contact adhesive would mainly be limited by the compatability of the adhesive with the SML component of the drug delivery system.

In the embodiments of FIGS. 1 and 2 the carrier or matrix material has sufficient viscosity to maintain its shape without oozing or flowing. If the matrix or carrier is a low viscosity flowable material, the composition can be fully enclosed in a pouch or pocket between the impermeable backing and a permeable or microporous skin contacting membrane as known to the art from U.S. Pat. No. 4,379,454, noted above, for example. Although the invention is most useful with drugs whose permeability is too low for therapeutic effects to be obtained in the absence of an enhancer; its use with systems employing drug rate controlling membranes such as disclosed in U.S. Pat. Nos. 3,598,122 and 3,598,123 noted above is also contemplated.

EXAMPLE I

A transdermal therapeutic system as described with respect to FIG. 1 for administration of progesterone was formulated from 10% progesterone, 25% Sucrose Monococoate (Croda, Inc., N.J.), 27% Staybelite Ester #5 (Hercules, Inc.) tackifier and 38% EVA 40. The system was applied to human epidermis for 4 days and the progesterone flux measured. The flux through a first sample averaged 2.0 μg/cm²/hr and through a second sample averaged 3.8 μg/cm²/hr.

The same formulation was tested on a human subject by application of an 80 cm² patch. Measurement of the progesterone blood level after an 8 hour period indicated an increase in progesterone of 40 ng/dl.

EXAMPLE II

A transdermal therapeutic system for administration of hydromorphone was formulated from 25% hydromorphone, 25% sucrose monolaurate solids and 50% EVA 40. In vitro test results of two samples are compared to a control sample (25% hydromorphone and 75% EVA 40), in the following table:

TABLE I

| | DRUG FLUX, μg/cm²/hr | | | | | |
|---|---|---|---|---|---|---|
| TIME, hrs | 16.00 | 24.00 | 40.00 | 48.33 | 63.99 | 79.99 |
| Sample I | 8.83 | 15.86 | 21.11 | 30.04 | 28.30 | 14.21 |
| Sample II | 14.03 | 18.75 | 18.41 | 24.24 | 26.84 | 14.29 |
| Control | 3.53 | 5.18 | 5.12 | 5.11 | 6.15 | 3.99 |

EXAMPLE III

A transdermal therapeutic system for administration of levorphanol was formulated from 25% levorphanol, 25% SML solids and 50% EVA 40. In vitro test results of two samples are shown in the following table:

TABLE II

| | DRUG FLUX, μg/cm²/hr | | | | | |
|---|---|---|---|---|---|---|
| TIME, hrs | 16.00 | 24.00 | 40.00 | 48.33 | 63.99 | 79.99 |
| Sample I | 31.97 | 44.40 | 39.17 | 40.41 | 29.85 | 12.99 |
| Sample II | 24.69 | 38.63 | 39.41 | 41.49 | 35.42 | 15.02 |

EXAMPLE IV

A transdermal therapeutic system as described with respect to FIG. 1 for administration of progesterone was formulated from 5.0% progesterone, 20.0% SML, 40.5% EVA 46 and 34.5% Staybelite Ester #5. This was tested simultaneously with a system for the administration of estradiol having the same formulation except for the drug, which was estradiol valerate instead of progesterone.

Measurement of the plasma progesterone and estradiol levels after a 24 hour period indicated an increase in progesterone of 44 ng/dl and in estradiol of 0.8 ng/dl.

Having thus generally described our invention and having provided specific embodiments thereof it will be readily apparent to workers skilled in the art that various modifications and substitutions can be made without departing from the scope of this invention which is limited only to the following claims.

We claim:

1. A method for enhancing the transdermal flux of a biologically active agent through intact skin which comprises placing a source of said agent in agent transmitting relationship to said intact skin in the presence of a permeation enhancing amount of a permeation enhancer consisting essentially of a sucrose monolaurate mixed with sucrose esters of coconut fatty acids.

2. The method of claim 1 wherein the source of said agent contains agent in excess of its saturation concentration in said source.

3. In a method for transdermally administering a biologically active agent by permeation through skin which comprises:

(a) placing a source of said agent and a permeation enhancer therefor in agent and permeation enhancer transmitting relationship to said skin, and (b) maintaining said source in contact with said skin for a period of time sufficient to produce a beneficial effect; the improvements wherein said permeation enhancer consists essentially of a material selected from the group consisting of sucrose monolaurate mixed with sucrose esters of coconut fatty acids.

* * * * *